(12) United States Patent
Mestres Armengol et al.

(10) Patent No.: US 9,351,591 B2
(45) Date of Patent: May 31, 2016

(54) EXPANDER DEVICE FOR KEEPING A DISPLAY DEVICE ERECT

(71) Applicant: Ferran Mestres Armengol, Sant Just Desvern (Barcelona) (ES)

(72) Inventors: Ferran Mestres Armengol, Sant Just Desvern (ES); Francisco López Fernández, Sant Just Desvern (ES)

(73) Assignee: Ferran Mestres Armengol, Barcelona (ES)

( * ) Notice: Subject to any disclaimer, the term of this patent is extended or adjusted under 35 U.S.C. 154(b) by 0 days.

(21) Appl. No.: 14/720,863

(22) Filed: May 25, 2015

(65) Prior Publication Data

US 2015/0265070 A1    Sep. 24, 2015

Related U.S. Application Data

(63) Continuation of application No. PCT/ES2013/000261, filed on Nov. 22, 2013.

(30) Foreign Application Priority Data

Nov. 28, 2012  (ES) .................................. 201201202

(51) Int. Cl.
*A45D 19/04*  (2006.01)
*A47F 5/11*   (2006.01)
*A61B 10/02*  (2006.01)
(Continued)

(52) U.S. Cl.
CPC .............. *A47F 5/112* (2013.01); *A61B 10/0241* (2013.01); *A61B 10/0275* (2013.01); *A61L 31/088* (2013.01); *A61L 31/16* (2013.01); *A61M 37/00* (2013.01); *A61N 1/0502* (2013.01); *F16B 12/00* (2013.01); *A47F 5/11* (2013.01); *A61B 2010/009* (2013.01);
(Continued)

(58) Field of Classification Search
CPC ....... A47F 5/112; A47F 5/11; A61B 10/0275; A61B 2010/009; A61N 1/05012; F16B 12/00
See application file for complete search history.

(56) References Cited

U.S. PATENT DOCUMENTS 8,167,255 B2 *   5/2012   Tzuo ...................... A47B 43/02
                                                            211/149
2005/0279906 A1  12/2005  Moss et al.
2010/0236117 A1   9/2010  Mestres Armengol et al.

FOREIGN PATENT DOCUMENTS

EP       1950723 A2     7/2008
EP       2201867 A2     6/2010
(Continued)

*Primary Examiner* — Amy Sterling
(74) *Attorney, Agent, or Firm* — Hess Patent Law Firm LLC; Robert J. Hess

(57) ABSTRACT

The expanding device (200) comprises a plate (20) connected internally to at least one panel of the display and divided by a first hinge into first and second plate portions (20a, 20b). An elastic tensile element (7) pulls the first and second plate portions (20a, 20b) to fold the plate (20) around the first hinge from a flat folded position to an angled working position. A limiting member (23) is hingedly connected to the first plate portion (20a) by a second hinge (22) and is provided with a free edge (23a) which, when the plate (20) is in an angled working position, is in contact with the second plate portion (20b) in order to limit the folding of the plate (20) to the angled working position. The second hinge (22) forms an angle greater than zero degrees with respect to the first hinge.

19 Claims, 7 Drawing Sheets

(51) Int. Cl.
  *A61N 1/05* (2006.01)
  *F16B 12/00* (2006.01)
  *A61L 31/08* (2006.01)
  *A61L 31/16* (2006.01)
  *A61M 37/00* (2006.01)
  *A61B 10/00* (2006.01)
  *A61B 17/00* (2006.01)

(52) U.S. Cl.
  CPC . *A61B 2017/00889* (2013.01); *A61L 2300/404* (2013.01); *A61L 2300/606* (2013.01)

(56) References Cited

FOREIGN PATENT DOCUMENTS

| FR | 2257971 A2 | 8/1975 |
| WO | 2006/067252 A1 | 6/2006 |
| WO | 2010/018272 A1 | 2/2010 |
| WO | 2014/083216 | 6/2014 |

* cited by examiner

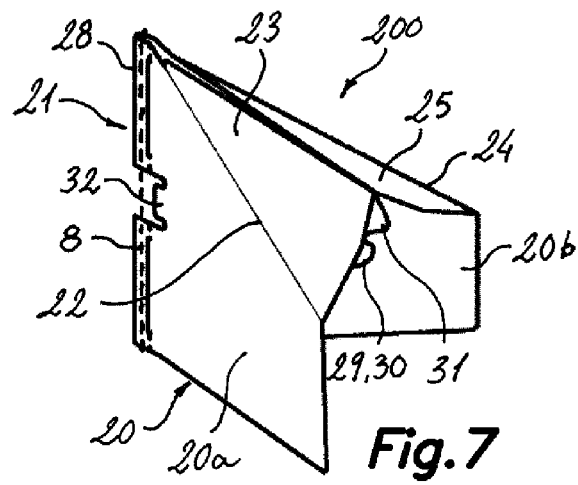
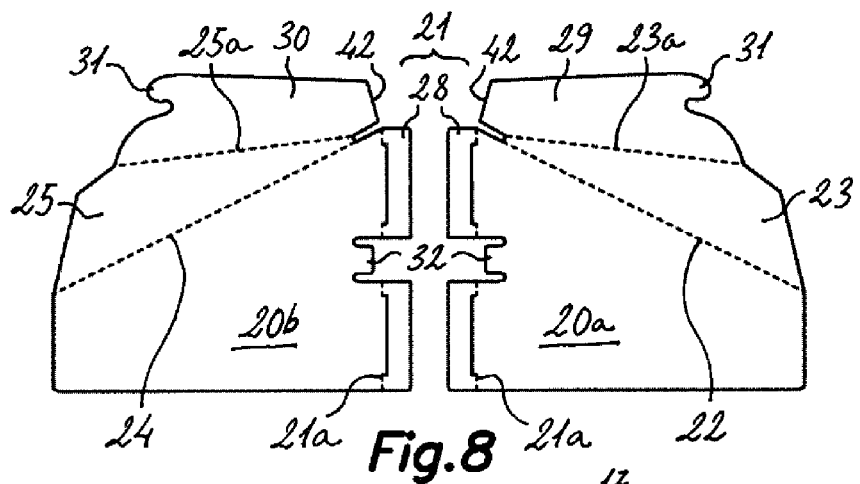
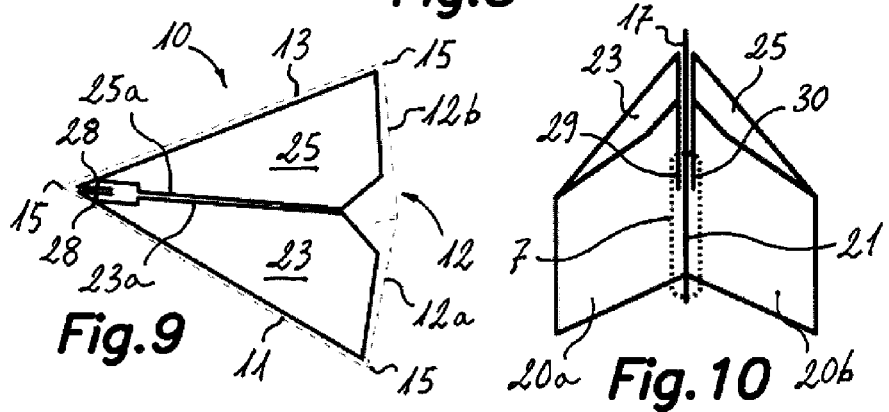

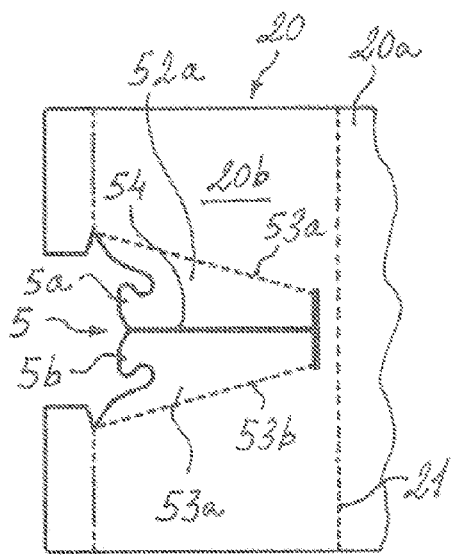
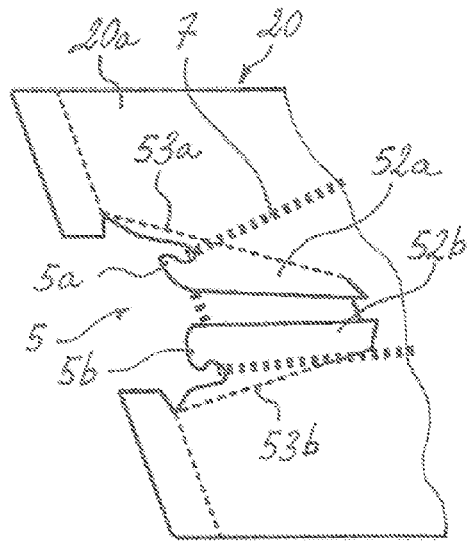
Fig. 12  Fig. 13
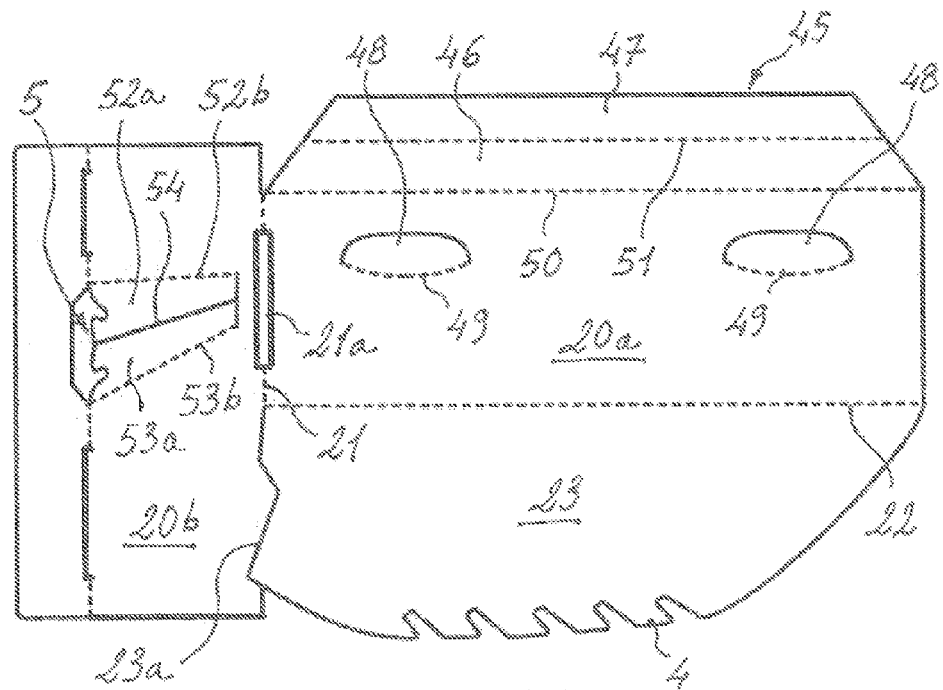
Fig. 14

EXPANDER DEVICE FOR KEEPING A DISPLAY DEVICE ERECT

TECHNICAL FIELD

The present invention relates to a display, which has three or more flat panels provided with lateral edges connected to one another forming corners and a foldable expander used for maintaining the display upright, wherein the expanding device is located between two of these flat panels in order to push them from within from a collapsed position into an expanded position, in which the flat panels have a three dimensional arrangement capable of being held upright.

BACKGROUND OF THE INVENTION

The document, WO 2006/067252 A1 makes known an expanding device for expanding a self-expandable foldable display, the display having two panels connected to one another by their lateral edges. The mentioned expanding device comprises a plate divided by a first hinge into first and second plate portions, at least one of which is connected to at least one panel of the display. An elastic tensile element is provided for pulling the first and second plate portions towards each other to fold the plate around said first hinge from a flat folded position to an angled working position. The plate comprises a limiting member, which has a connection edge connected by a second hinge to the first plate portion and a free edge, which, when the plate is in said angled working position, is in contact with the second plate portion in order to limit the folding of the plate to an angled working position. However, in this expanding device, the second hinge is parallel to the first hinge and the panels of the display are not flat panels, but in the expanded position, they are pushed from within outwards by the expanding device and adopt a bulged convex arrangement.

The document, WO 2010/018272 A1 describes an expanding device comprising two or more plates made from cardboard sheet or another similar material cooperating with one or more elastic tensile elements, which may be applied to maintain upright a display formed by one single flat panel or to expand a self-expandable foldable display made of three or more cardboard panels or other similar material connected by their lateral edges from a collapsed position to an expanded position capable of being maintained upright. However, this expanding device, when it is used with the display formed by one single flat panel, has the drawback that the one or plurality of elastic tensile elements and its hook elements are exposed and are visible in the working position and when it is used with the self-expandable foldable display made of three or more panels connected by their lateral edges, it has the drawback that the plates of the expanding device are not superimposed upon interior surfaces of the flat panels of the display and do not act as reinforcing plates for these flat panels of the display.

DISCLOSURE OF THE INVENTION

The present invention contributes to overcoming and mitigating the previous and other drawbacks, providing a display having an expanding device for maintaining the display upright The expanding device of the present invention comprises a plate which has a first hinge which divides said plate into first and second plate portions, at least one of which is connected to at least one panel of the display, an elastic tensile element provided for pulling said first and second plate portions towards each other to fold the plate around said first hinge from a folded flat position to an angled working position and at least one limiting member which has a connection edge hingedly connected to a first plate portion by a second hinge and a free edge which, when the plate is in said angled working position, is in contact with the second plate portion in order to limit the folding of the plate to an angled working position.

In the expanding device, the mentioned second hinge forms an angle greater than zero degrees with respect to said first hinge or in other words, it is inclined or is perpendicular with respect to said first hinge. Thus, by virtue of the mentioned angle between the first and second hinges, when the expanding device is in the angled working position, the limiting member and the first plate portion form a dihedral angle which has a ridge along the second hinge, and this ridge, since it is traversal to the first hinge, reinforces the first plate portion against undesired bending in directions parallel to the first hinge.

In one embodiment, the expanding device of the present invention is applied to a display provided with three or more flat panels, which have lateral edges connected to one another forming the corners of a hollow prismatic body. In such case, the expanding device is located between at least two of the mentioned flat panels of the display for pushing from within the flat panels from a collapsed position, in which the flat panels are mutually superimposed and have a flat arrangement, to an expanded position, in which the flat panels have a three dimensional arrangement capable of being held upright.

In the prismatic display, the first hinge of the plate is arranged internally in one of the mentioned corners of the display and substantially aligned with two of the lateral edges connected to one another of two of the adjacent flat panels, which form this corner of the display. The first and second plate portions of the expanding device are superimposed internally upon these two adjacent flat panels, which form this corner of the display. Thus the first and second plate portions of the plate of the expanding device, which is made of relatively strong cardboard sheet, internally support the flat panels of the display, reinforce them and contribute in such a way that the same are maintained flat in spite of being made from a relatively thin cardboard sheet.

In this embodiment, the limiting member preferably has one or more first hook elements formed therein and the first plate portion has one or more second hook elements formed therein. The mentioned elastic tensile element is an elastic tensile ring hooked on said first and second hook elements. Optionally, the limiting member has a plurality of first hook elements formed therein and located at different distances from the first hinge and/or the first plate portion has a plurality of second hook elements formed therein and located at different distances from the first hinge, such that the first and/or second hook elements can be selected at the time of hooking the elastic tensile element with the aim of regulating the tension of the elastic tensile element.

In another embodiment, the plate comprises, in addition to the first limiting member described above, a second limiting member which has a connection edge hingedly connected to the second plate portion by a third hinge which forms an angle greater than zero degrees with respect to said first hinge, that is to say, which is inclined or is perpendicular with respect to the first hinge, and a second free edge which, when the plate is in the angled working position, interacts with the first free edge of the first limiting member in order to limit the folding of the plate to the angled working position. Preferably, the first and second free edges of the first and second limiting members are mutually crossed and are supported on each other when the plate is folded in the angled working position.

In this case, the first limiting member has one or more first hook elements formed therein, the second limiting member has one or more second hook elements formed therein and the elastic tensile element is an elastic tensile ring hooked on said first and second hook elements. Preferably, the first limiting member has a plurality of the first hook elements formed therein and located at different distances from the first hinge and/or the second limiting member has a plurality of second hook elements formed therein and located at different distances from the first hinge, such that the first and/or second hook elements can be selected at the time of hooking the elastic tensile element with the aim of regulating the tension of the elastic tensile element.

Given that the plate of the expanding device is made preferably of cardboard sheet or another similar material, the first, second and third hinges can be easily proportioned by groove lines. Optionally, the groove lines can be combined with cut sections to facilitate the folding of the sheet.

With the aim of connecting the expanding device to the display, in one embodiment, the first and second plate portions of the plate of the expanding device are joined, for example by adhesive, to interior surfaces of two of the adjacent flat panels of the display.

In another embodiment, the first plate portion of the plate of the expanding device has a first end edge opposite to the first hinge connected to a corner of the display formed by the lateral edges of two of the adjacent flat panels of the display and the second plate portion of the plate of the expanding device has a second end edge opposite to the first hinge connected to another corner of the display formed by the lateral edges of another two of the adjacent flat panels of the display.

To this end, the mentioned first and second end edges of the first and second plate portions are hingedly connected to respective connection tabs and an elastic connector ring is provided surrounding said connection tabs of the plate and inwardly-bent tabs hingedly connected to the lateral edges of the panels of the display. The fact of connecting the lateral edges of the panels of the display by means of inwardly-bent tabs and elastic connector rings arranged surrounding these inwardly-bent tabs is conventional in the field of self-expandable foldable displays.

Preferably, the connection tabs of the plate have substantially the same length in the direction of height of the display as said inwardly-bent tabs of the flat panels of the display for ensuring a secure fastening. In a particular embodiment, the first and second end edges of the first and second plate portions are hingedly connected to the respective connection tabs by groove lines in combination with cut lines which define separating members which are coplanar with the respective first and second plate portions and which project further from the first and second end edges when the connection tabs are folded. Thus, the mentioned separating members maintain the first and second end edges of the first and second plate portions slightly distanced from the bottom of the corners of the display preventing excessive superimposing of thicknesses of cardboard sheet.

In another embodiment, the first and second free edges of the first and second limiting members are mutually aligned and hingedly connected to one another. For example, the first and second plate portions can be separate pieces, which have respective adjacent edges hingedly connected to one another to form the first hinge. The articulated connection between these first and second adjacent edges of the first and second plate portions can be realized by respective connection tabs hingedly connected to the first and second adjacent edges and an elastic connector ring provided surrounding said connection tabs of the plate and inwardly-bent tabs hingedly connected to the lateral edges of the panels of the display.

The first and second free edges of the first and second limiting members can be hingedly connected to respective connection tabs which have respective superimposed opposing surfaces and respective superimposed first hook elements and the mentioned elastic tensile element can be an elastic tensile ring hooked on said superimposed first hook elements, which maintains the first and second limiting members together, and on at least one second hook element formed on at least one of the first and second plate portions or on at least one of the inwardly-bent tabs of the panels of the display.

The flat panels of the prismatic display to which the expanding device is applied can have one or more transversal fold lines, which divide them into various superimposed sections, and the prismatic display can be folded around these transversal fold lines from the collapsed position to a compact folded position. In such case, there can be one or more expanding devices of the present invention arranged between the flat panels on various or each of the superimposed sections of the same.

The mentioned compact folded position of the display is stable since the folds of the flat panels counteract the tension exerted by the elastic tensile elements of the expanding devices. When, from the compact folded position, an unfolding movement of the display is manually initiated, the tension exerted by the elastic tensile elements automatically expands the expanding devices, which push the flat panels from within to expand the display rapidly to the expanded position.

BRIEF DESCRIPTION OF THE DRAWINGS

The previous and other features and advantages will become more evident from the following detailed description of exemplary embodiments with reference to the attached drawings, in which:

FIG. 7 is a perspective view of an expanding device for maintaining upright a display according to yet another embodiment of the present invention, in an angled working position;

FIG. 8 is a plan view of a plate composed of two separated plate portions which forms part of the expanding device of FIG. 7, in a flat position;

FIG. 9 is a top view of the expanding device of FIG. 7 applied to a triangular prismatic display;

FIG. 10 is a frontal view of the expanding device of FIG. 7 applied to a triangular prismatic display;

FIG. 12 is a partial plan view of a plate which forms part of an expanding device according to another additional embodiment of the present invention, showing a second hook element;

FIG. 13 is a partial perspective view of the plate of FIG. 12 with one elastic tensile element connected to the second hook element;

FIG. 14 is a plan view of a plate including a variant of the second hook element of FIGS. 12 and 13, in a flat position.

DETAILED DESCRIPTION OF EXEMPLARY EMBODIMENTS

Figure 1:
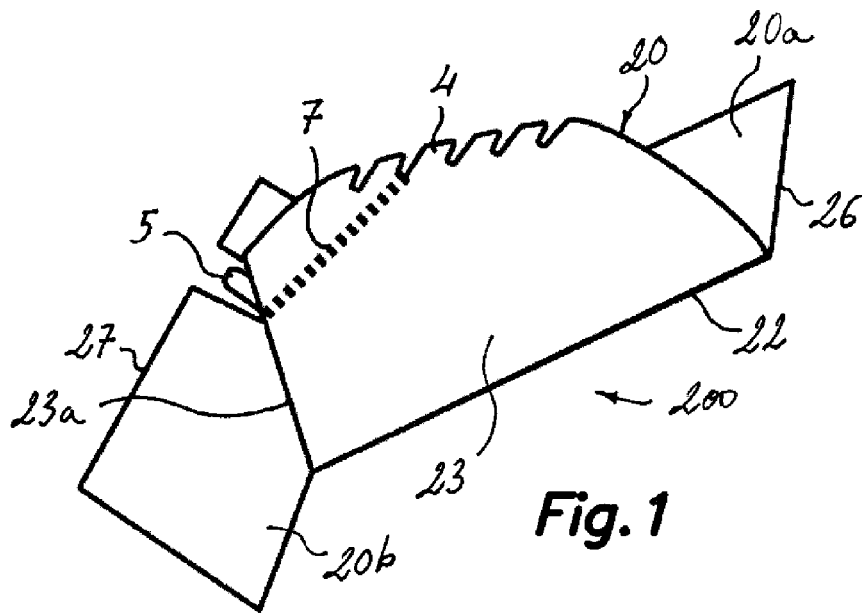
FIG. 1 is a perspective view of an expanding device for maintaining upright a display according to an embodiment of the present invention, in an angled working position.
Figure 2:
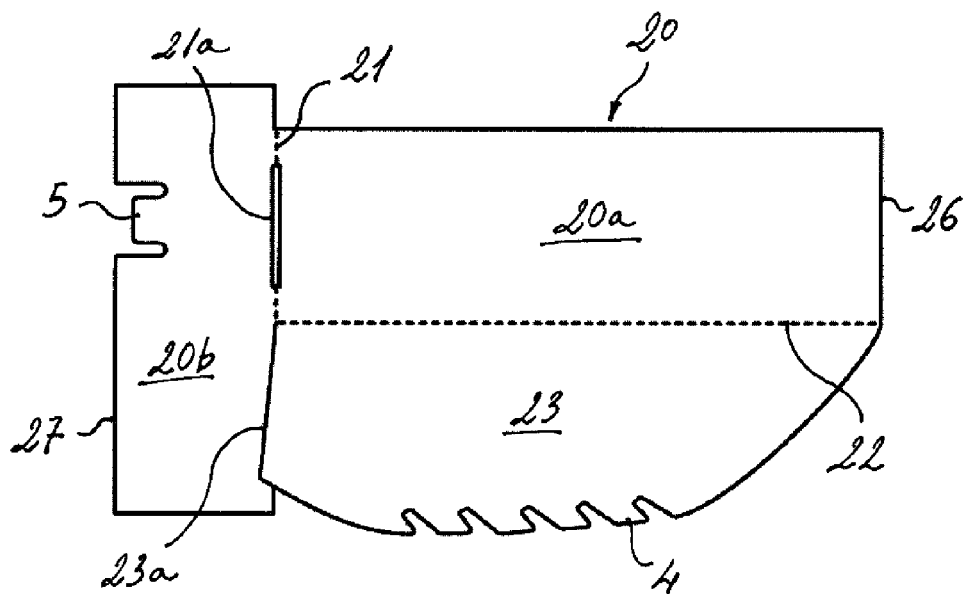
FIG. 2 is a plan view of a plate which forms part of the expanding device of FIG. 1, in a flat position.
Figure 3:
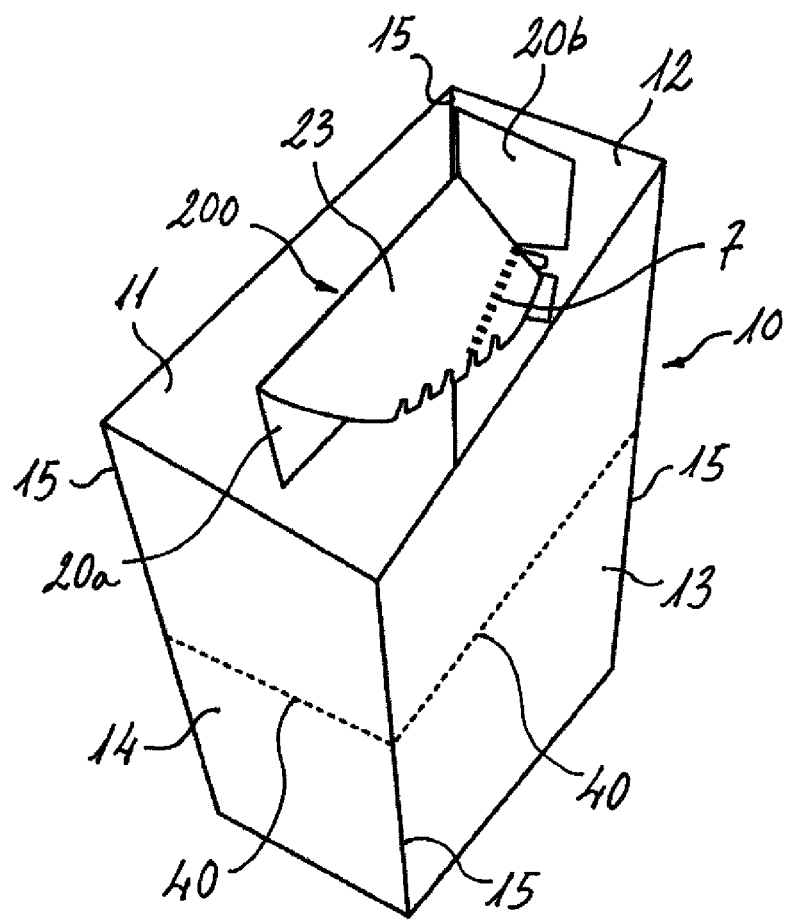
FIG. 3 is a perspective view of the expanding device of FIG. 1 applied to a rectangular prismatic display.

Firstly making reference to the FIGS. 1 to 3, the reference numeral 200 designates in general an expanding device, which can be applied to maintain upright a display 10, as FIG. 3 shows. The display 10 is a conventional type of display which comprises four flat panels 11, 12, 13, 14 hingedly connected to one another by their lateral edges 15 such that the display 10 can adopt a collapsed position (not shown) in which the flat panels 11, 12, 13, 14 are superimposed and have a flat arrangement and an expanded position (FIG. 3) in which the flat panels 11, 12, 13, 14 have a three dimensional arrangement capable of being held upright.

In the example shown in FIG. 3, the display 10 has a rectangular prismatic arrangement when it is in the expanded position due to the four flat panels 11, 12, 13, 14 composing it. The display 10 can be made, for example, of one or various pieces of cardboard sheet or similar material.

The expanding device 200 as shown in FIG. 1 comprises a plate 20 and an elastic tensile element 7. The plate 20 (shown separately in FIG. 2) has a first hinge 21 which divides said plate 20 into first and second plate portions 20a, 20b and a limiting member 23 which has a connection edge hingedly connected to the first plate portion 20a by a second hinge 22 substantially perpendicular to the first hinge 21.

The first plate portion 20a has a first end edge 26 opposite to the first hinge 21 and the second plate portion 20b has a second end edge 27 opposite to the first hinge 21. The mentioned limiting member 23 has a free edge 23a and a plurality of hook elements 4 formed on another edge of the same while the second plate portion 20b has a second hook element 5 formed on said second edge of the same. The plate 20 is preferably made of a piece of cardboard sheet or similar material formed by stamping and the first and second hinges 21, 22 are formed by means of groove lines.

Eventually, the groove lines which form the hinges, such as for example the first hinge 21 of the plate 20 of FIG. 1, are combined with one or more cut lines 21a to additionally facilitate the folding of the plate 20.

In the embodiment shown in FIGS. 1 to 3, the elastic tensile element 7 is an elastic tensile ring, which, in an operative situation (FIG. 1) is hooked on said first and second hook elements 4, 5 such that it pulls the limiting member 23 towards the second plate portion 20b and, given that the limiting member 23 is connected to the first plate portion 20a, the elastic tensile element 7 pulls the first and second plate portions 20a, 20b towards each other. With this, the plate 20 is folded around said first and second hinges 21, 22 from a flat folded position (not shown) to an angled working position (FIG. 1).

The tension exerted by the elastic tensile element 7 can be regulated selecting a first hook element 4, from among the mentioned plurality of first hook elements 4, where the elastic tensile element 7 hooks, given that this plurality of first hook elements 4 is located at different distances from the second hook element 5.

When the plate 20 is in the mentioned angled working position shown in FIG. 1, the free edge 23a of the limiting member 23 abuts against a surface of the second plate portion 20b and with this the folding of the plate 20 is limited to the angled working position. The geometry of the plate 20 for the particular embodiment shown in the FIGS. 1 to 3 is designed such that in the angled working position, the first and second plate portions 20a, 20b together form a dihedral angle of approximately 90 degree useful for a rectangular prismatic display. However, a person skilled in the art understands that by varying the angle between the first and second hinges 21, 22, the angle between the first free edge 23a of the limiting member 23 and the first hinge 21 and the relative positions between the first and second hook elements 4, 5, dihedral angles different from 90 degrees can be determined between the first and second plate portions 20a, 20b, for example, dihedral angles of approximately 60 degrees, useful for an equilateral triangular prismatic display, dihedral angles of approximately 72 degrees, useful for a pentagonal prismatic display, dihedral angles of approximately 120 degrees, useful for a hexagonal prismatic display and any other dihedral angles.

As shown in FIG. 3, in an operative situation, the expanding device 200 is located between two of the adjacent flat panels 11, 12 of the rectangular prismatic display 10, which form a corner. The first hinge 21 of the plate 20 is arranged internally in this corner of the display 10, substantially aligned with the lateral edges 15 connected to one another of these two adjacent flat panels 11, 12. Furthermore, the first and second plate portions 20a, 20b of the plate 20 are superimposed internally upon the two adjacent flat panels 11, 12, 13, 14 which form this corner of the display 10.

In the particular embodiment shown in FIGS. 1 to 3, the first and second plate portions 20a, 20b are joined, for example by means of an adhesive, to the internal surfaces of the two corresponding adjacent flat panels 11, 12 of the display 10 which form the corner where the expanding device 200 is arranged. Thus, the first and second plate portions 20a, 20b reinforce the flat panels 11, 12 of the display and help to maintain them flat, thanks to which the flat panels 11, 12, 13, 14 of the display 10 can be manufactured by means of a cardboard sheet or other relatively thin similar material.

Obviously, when the display 10 is in the mentioned collapsed position (not shown) the expanding device 200 is in the flat folded position. Due to the effect of the tension produced by the elastic tensile element 7, the expanding device 200 tends to adopt the angled working position and pushes from within the flat panels 11, 12, 13, 14 of the display 10 automatically expanding it from the collapsed position to the expanded position (FIG. 3).

In a conventional manner, the flat panels 11, 12, 13, 14 of the prismatic display 10 of FIG. 3, have transversal fold lines 40 which divide them into various superimposed sections, such that the display 10 can be folded around these transversal fold lines 40 from the collapsed position to a compact folded position. In such case, there can be one or more expanding devices 200 of the present invention arranged between the flat panels 11, 12, 13, 14 in various or in each of the superimposed sections of the same.

The display 10 is maintained stable while it is in the mentioned compact folded position, since the folds of the superimposed sections of the flat panels around the transversal fold lines 40 counteract the tension exerted by the elastic tensile elements 7 of the expanding devices 200. However, when, from the compact folded position, an unfolding movement of the display 10 is manually initiated, the tension exerted by the elastic tensile elements 7 automatically expands the expanding devices 200 and the latter push the flat panels 11, 12, 13, 14 from within to expand the display 10 rapidly to the expanded position.

Figure 4:
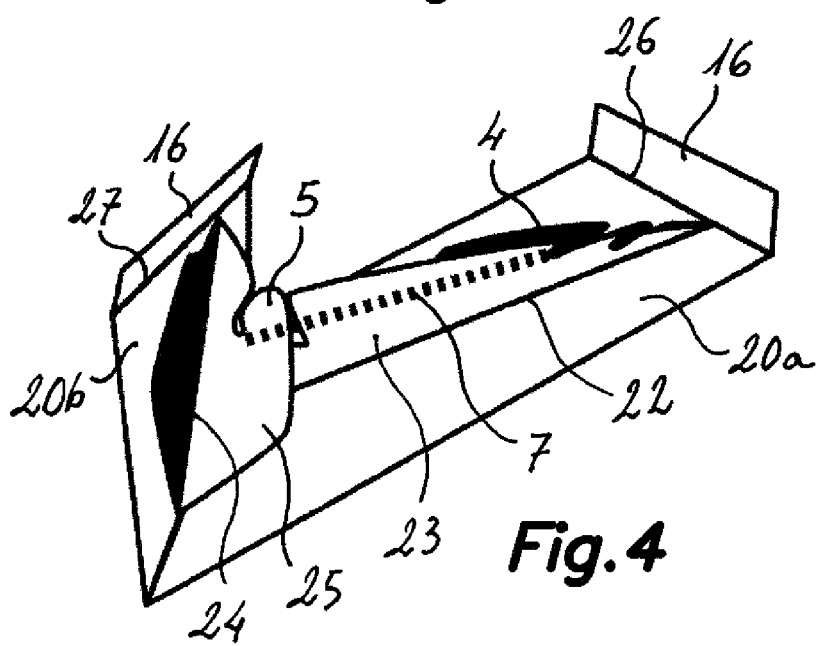
FIG. 4 is a perspective view of an expanding device for maintaining upright a display according to another embodiment of the present invention, in an angled working position.
Figure 5:
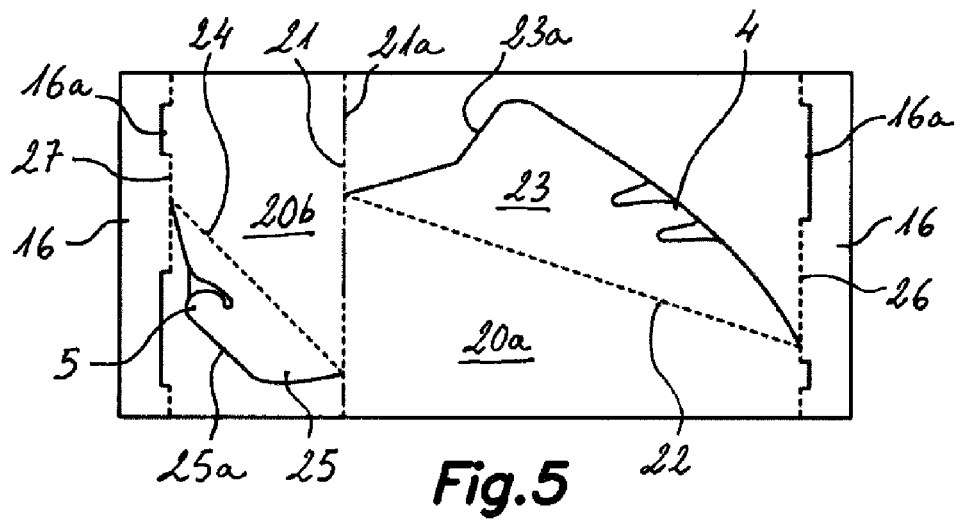
FIG. 5 is a plan view of a plate which forms part of the expanding device of FIG. 4, in a flat position.
Figure 6:
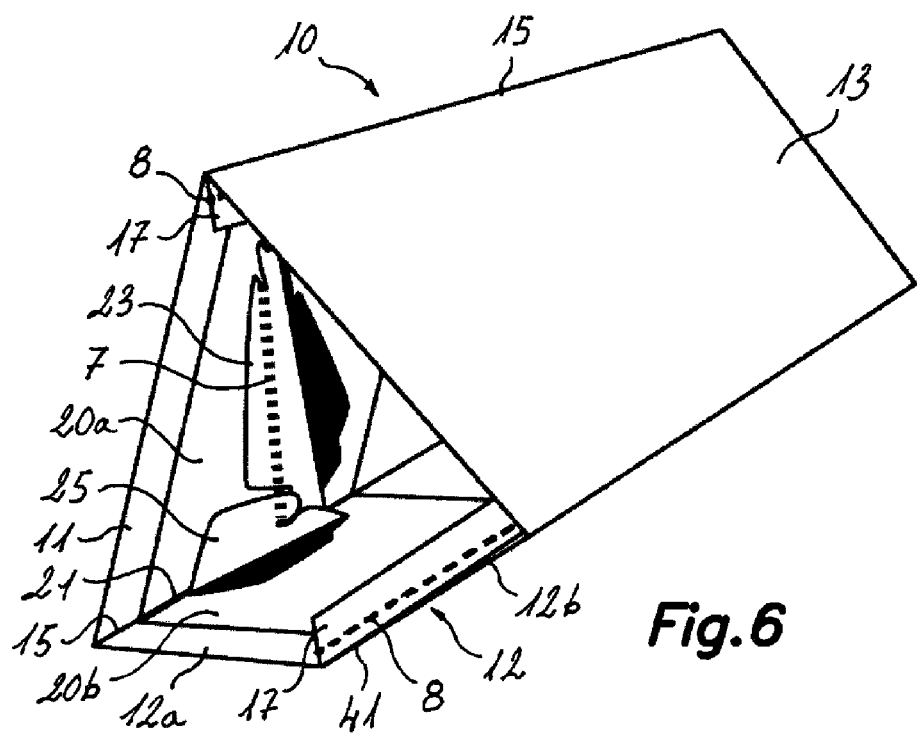
FIG. 6 is a perspective view of the expanding device of FIG. 4 applied to a triangular prismatic display.

FIGS. 4, 5 and 6 show another embodiment of the expanding device 200 of the present invention, which is in all analogous to the embodiment previously described in relation to FIGS. 1, 2 and 3, except in that here, instead of one single limiting member 23, the plate 20 (shown separately in FIG. 5) includes a first limiting member 23 and a second limiting member 25.

The mentioned first limiting member 23 has a connection edge hingedly connected to the second plate portion 20b by a second hinge 22, which in this case forms an angle greater than zero degrees and less than 90 degrees with respect to the first hinge 21 and a first free edge 23a while the second limiting member 25 has a connection edge hingedly connected to the second plate portion 20b by a third hinge 24 which at the same time forms an angle greater than zero degrees and less than 90 degrees with respect to said first hinge 21 and a second free edge 25a. The angles between the second and third hinges 22, 24 and the first hinge 21, respectively, are variable and alternatively one of them can even become equal to 90 degrees.

On the first limiting member 23 are formed a plurality of first hook elements 4 and on the second limiting member 25 is formed a second hook element 5. The elastic tensile element 7 (FIG. 4) is an elastic tensile ring hooked on one of said first hook elements 4 and on the second hook element 5. The plurality of first hook elements 4 are arranged at different distances from the second hook element 5 such that one of the first hook elements 4 can be selected for hooking the elastic tensile element 7 with the aim of regulating the tension exerted by the same.

Thus the tension exerted by the elastic tensile element 7 pulls the first and second limiting members 23, 25 towards each other, folding them around their respective second and third hinges 22, 24 and, given that the first and second limiting members 23, 25 are connected to the first and second plate portions 20a, 20b respectively, the tension exerted by the elastic tensile element 7 pulls the first and second plate portions 20a, 20b towards each other, folding the plate 20 around the first hinge 21 towards the angled working position shown in FIG. 4. When the plate 20 is folded into the angled working position, the first and second free edges 23a, 25a of said first and second limiting members 23, 25 are mutually crossed and are supported on each other, limiting a further folding of the plate 20.

On the plate 20 shown in FIG. 5, the first and second end edges 26, 27 of the first and second plate portions 20a, 20b are hingedly connected to respective connection tabs 16. The articulated connection between the first and second end edges 26, 27 and the respective connection tabs 16 is formed by groove lines in combination with cut lines having off-set sections defining separating members 16a which are coplanar with the respective first and second plate portions 20a, 20b. The function of these separating members 16a is explained below.

FIG. 6 shows the expanding device of FIG. 4 applied to a display 10 of a conventional type, which in this example comprises first, second and third flat panels 11, 12, 13 hingedly connected to one another by their lateral edges 15, where one of the flat panels, for example the second flat panel 12 has a longitudinal hinge 41 which divides it into two adjacent panel sections 12a, 12b such that the display 10 can adopt a collapsed position (not shown) in which the flat panels 11, 12, 13 are superimposed and have a flat arrangement, and an expanded position (FIG. 6) in which the first, second and third flat panels 11, 12, 13 have a three dimensional arrangement capable of being held upright.

The display 10 of FIG. 6 has a triangular prismatic arrangement when it is in the expanded position due to the three flat panels 11, 12, 13 composing it. In the particular example illustrated in FIG. 6, the display 10 is made of two pieces of cardboard sheet or similar material, where one of said pieces includes the first flat panel 11 and one of the panel sections 12a of the second flat panel 12, and the other of the pieces includes the third flat panel 13 and the other of the panel sections 12b of the second flat panel 12. The two pieces of cardboard sheet or similar material have their lateral edges hingedly connected to inwardly-bent tabs 17 mutually superimposed and surrounded by elastic connector rings 8 which maintain the two pieces joined together.

The expanding device 200 is located between the first flat panel 11 and one of the panel sections 12a of the second flat panel 12, with the first hinge 21 arranged internally adjacent to and aligned with the corner formed by the adjacent lateral edges 15 of the first and second flat panels 11, 12 and with the connection tabs 16 extending from the first and second folded end edges 26, 27 bent, superimposed upon the inwardly-bent tabs 17 extending from the lateral edges of the first and second pieces of cardboard or similar material which form the flat panels 10, 11, 12 of the display 10, and surrounded by said elastic connector rings 8 such that the expanding device 200 is fastened to the display 10 by the elastic connector rings 8.

When the connection tabs 16 of the expanding device 200 are folded, the separating members 16a remain coplanar with the respective first and second plate portions 20a, 20b such that they project further from the first and second end edges 26, 27 and abut against the bottom of the corners of the display 10 and maintain the first and second end edges 26, 27 of the first and second plate portions 20a, 20b slightly distanced from the bottom of the corners of the display to prevent excessive superimposing of cardboard sheet thicknesses which could make the folding of the display into the collapsed position difficult.

Preferably the connection tabs 16 of the plate 20 have substantially the same length in the direction of the height of the display as said inwardly-bent tabs 17 of the flat panels 11, 12, 13, 14 of the display 10, although it is not an essential condition, especially when the flat panels 11, 12, 13, 14 are divided into various superimposed sections by transversal fold lines 40.

FIGS. 7 to 11 show yet another embodiment of the expanding device 200 useful for being applied in general to a prismatic display 10, and more particularly to a triangular prismatic display 10 analogous to that described above in relation to FIG. 6.

In essence, the expanding device 200 shown in FIGS. 7 to 11 is in all analogous to that described above in relation to FIGS. 4 to 6 except in that here the first and second plate portions 20a, 20b of the plate 20 are separate pieces (FIG. 8), which have respective adjacent edges 21a, 21b which in an operative situation are hingedly connected to one another in order to form the first hinge 21. Furthermore, in this embodiment, the first and second free edges 23a, 25a of the first and second limiting members 23, 25 are mutually aligned and hingedly connected to one another in an operative situation (FIG. 7). Preferably, the two pieces, which form the first and second plate portions 20a, 20b of the plate 20, are identical and are arranged symmetrically.

For the mutual connection of the two pieces which form the first and second plate portions 20a, 20b of the plate 20, the mentioned first and second adjacent edges 21a, 21b of the first and second plate portions 20a, 20b are hingedly connected to respective connection tabs 28 and an elastic connector ring 8 (FIG. 7) is arranged surrounding said connection tabs 28 of the plate 20. When the expanding device is installed on the display 10 (FIGS. 9 and 11), the connection tabs 28 of the expanding device 200 are superimposed upon the mentioned inwardly-bent tabs 17 extending from the lateral edges of the pieces of cardboard or similar material which form the panels 11, 12, 13 of the display 10 such that the elastic connector ring 8 fastens the expanding device 200 to the display 10.

For the connection of the first and second limiting members 23, 25, the first and second free edges 23a, 25a of the first and second limiting members 23, 25 are hingedly connected to respective connection tabs 29, 30, which have respective hook elements 31 formed at their ends furthest from the first hinge 21. In an operative situation, respective opposite surfaces of the mentioned connection tabs 29, 30 are superimposed and the respective first hook elements 31 are also superimposed. In this embodiment, the elastic tensile element 7 of the expanding device 200 is an elastic tensile ring (not shown in FIG. 7) hooked on said first hook elements 31 and on at least one of the second hook elements 32 formed on the first and second plate portions 20a, 20b.

Figure 11:
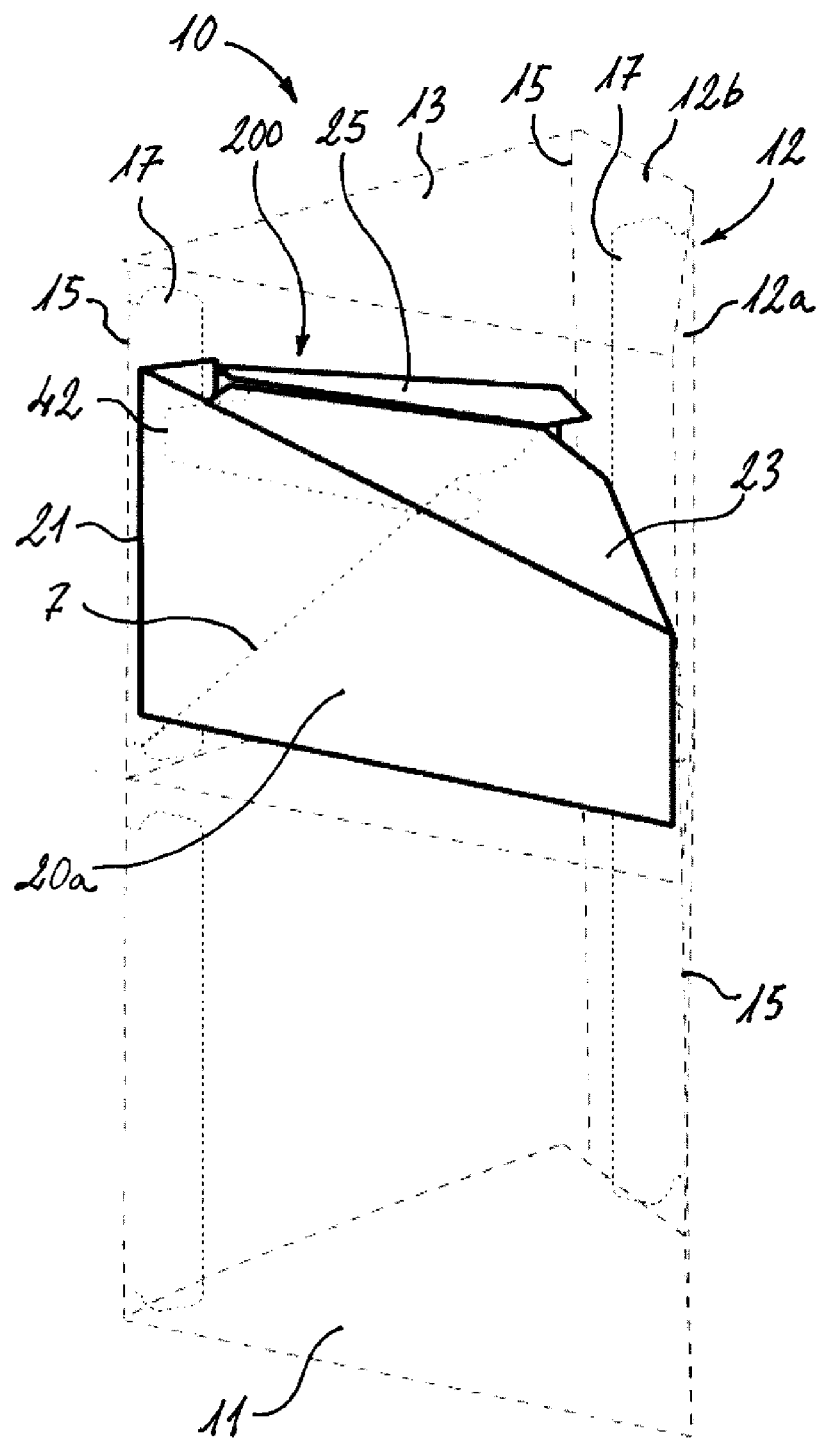
FIG. 11 is a perspective view of the expanding device of FIG. 7 applied to a triangular prismatic display.

Alternatively, as shown in FIGS. 10 and 11, the elastic tensile element 7 is hooked on the first hook elements 31 and on at least one of the inwardly-bent tabs 17 extending from the lateral edges of the pieces of cardboard or similar material which form the panels 11, 12, 13 of the display 10. In such case, the second hook elements 32 of the first and second plate portions 20a, 20b can be omitted.

In the flat folded position (not shown), both the first and second plate portions 20a, 20b as well as the first and second limiting members 23, 25 are mutually superimposed. The tension exerted by the elastic tensile element 7 pulls the first and second limiting members 23, 25 towards the first hinge 21, which forces the plate 20 to fold around the first hinge 21 separating the first and second plate portions 20a, 20b from each other and the first and second plate portions 20a, 20b push from within the flat panels 11, 12, 13 of the display 10 to expand the display from the collapsed position (not shown) to the expanded position (FIGS. 9 and 11).

In the triangular prismatic display, the expansion of the display 10 is limited by the two adjacent panel sections 12a, 12b of the flat panel 12 when both reach a coplanar position. In other prismatic displays, the expansion of the display 10 is limited by limiting stops 42 formed on ends of the connection tabs 29, 30 closest to the first hinge 21, which abut against the first hinge 21.

A person skilled in the art would understand that the plate 20 of the expanding device 200 of the embodiment described in relation to FIGS. 7 to 11 could be made of one single piece of cardboard or similar material connecting the first and second plate portions 20a, 20b by the first hinge 21 or alternatively connecting the first and second limiting members 23, 25 by their respective first and second free edges 23a, 25a.

In relation to FIGS. 12-15 another additional embodiment of the plate 20 is described, which is very similar to that described above in relation to FIGS. 1 and 2 except in the arrangement of the second hook element 5 and in the incorporation of a reinforcing profile 45 on one of its edges.

FIG. 12 shows the second plate portion 20b of the plate 20 connected to the first plate portion 20a by the first hinge 21 and the second hook element 5 formed on the second plate portion 20b. In this case, the second hook element 5 comprises two hook members 5a, 5b formed on edges of two contiguous fins 52a, 52b, which are separated by a dividing cut 54 and connected to the second plate portion 20b by respective opposing hooking hinges 53a, 53b, formed by respective groove lines. The mentioned dividing cut 54 is perpendicular to the first hinge 21 and the hooking hinges 53a, 53b are oblique with respect to the dividing cut 54 and diverge as they approximate the respective hook members 5a, 5b.

FIG. 13 shows the elastic tensile element 7 hooked on both hook members 5a, 5b of the second hook element 5 exerting pull on the second plate portion 20b of the plate 20. The tension of the elastic tensile element 7 causes a rotation of the two fins 52a, 52b around the respective hooking hinges 53a, 53b at the same time as it limits the rotation of the same in a working position. When the fins 52a, 52b are rotated in the working position, they form with the second plate portion 20b of the plate 20 respective dihedrals, which provide the second plate portion 20b with greater rigidity and resistance to bending and torsion.

FIG. 14 shows an entire plate 20 which includes first and second plate portions 20a, 20b connected to one another by a first hinge 21 and a limiting member 23 which has a connection edge hingedly connected to the first plate portion 20a by a second hinge 22 substantially perpendicular to the first hinge 21. The mentioned limiting member 23 has a free edge 23a and a plurality of hook elements 4 formed on another edge of the same opposing the second hinge. The second plate portion 20b has a second hook element 5 formed therein that is similar to that described above in relation to FIGS. 13 and 14, the only difference being that here the dividing cut 54 is not perpendicular to the first hinge 21 but rather is inclined towards the limiting member 23.

The plate 20 shown in FIG. 14 also comprises proximal and distal profiles fins 46, 47 arranged on a side of the plate portion 20a opposite to the limiting member 23 such that they extend substantially all along the length of the first plate portion 20a. Said proximal profile fin 46 is connected to the first plate portion 20a by a proximal hinge 50 parallel to the second hinge 22 and said distal profile fin 47 is connected to the proximal profile fin 46 by a distal hinge 51 parallel to the proximal hinge 50. In a region of the first plate portion 20a between the proximal hinge 50 and the second hinge 22 are formed a pair of tabs 48 connected to the first plate portion 20a by respective groove lines 49.

Figure 15:
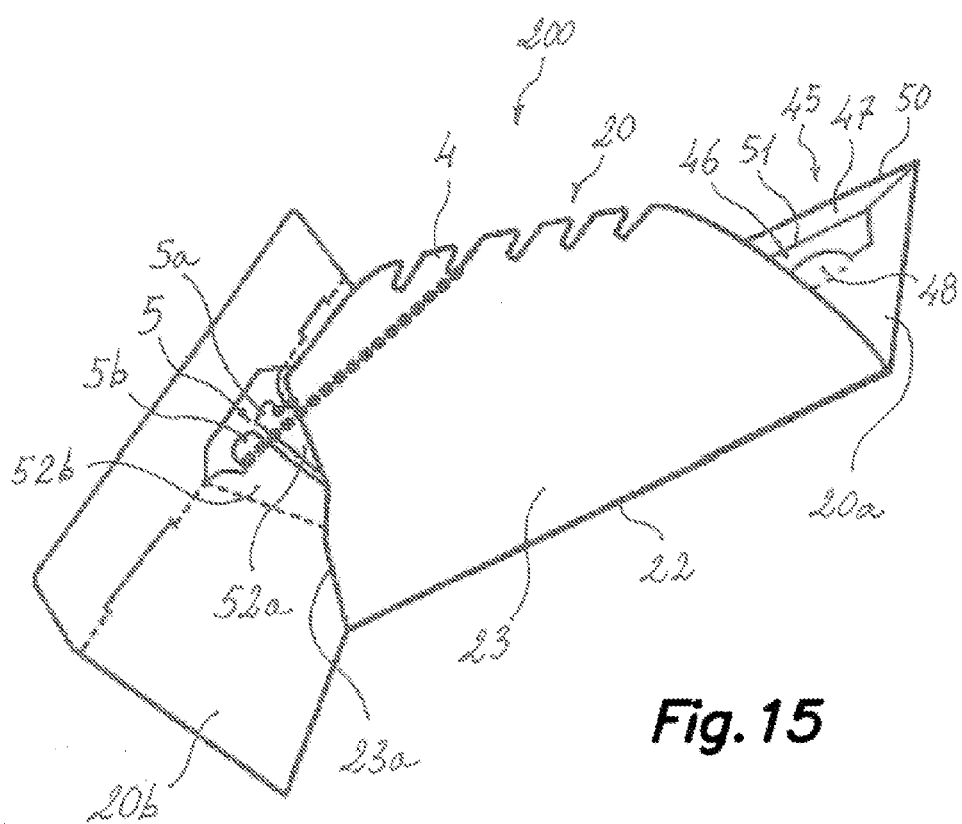
FIG. 15 is a perspective view of the plate of FIG. 14 in an angled working position in cooperation with an elastic tensile element forming an expanding device according to the present invention.

FIG. 15 shows the plate 20 of FIG. 14 folded in an angled working position in cooperation with an elastic tensile element 7 hooked on one of the hook elements 4 of the limiting member 23 and to both hook members 5a, 5b of the second hook element 5 of the second plate portion 20b forming an expanding device 200. In this angled working position, the limiting member 23 forms an acute angle with the first plate portion 20a and its free edge 23a makes contact with the second plate portion 20b limiting the rotation of the same. By virtue of the mentioned inclination of the dividing cut 54, the two fins 52a, 52b of the second hook element 5 are crossed with the free edge 23a of the limiting member 23 and the free edge 23a of the limiting member 23 has an angled outline which is coupled to the two fins 52a, 52b of the second hook element 5 in an angled working position.

Furthermore, in the angled working position shown in FIG. 15, the plate 20 shown in FIG. 14, the proximal and distal profile fins 46, 47 are folded around their respective proximal and distal hinges 50, 51 and a free edge of the distal profile fin 47 is coupled to the tabs 48, which are located at a distance from the proximal hinge 50 less than the sum of the widths of the proximal and distal profile fins 46, 47 such that they are in an angled position forming the mentioned reinforcing profile 45, which reinforces the edge of the first plate portion 20a opposite to the second hinge 22. The edge of the first plate portion 20a corresponding to the second hinge 22 is reinforced by the dihedral formed by the limiting member 23 and the first plate portion 20a in the angled working position.

It must be pointed out that the reinforcing profile 45 as has been described in relation to FIGS. 14 and 15 can be used for making rigid an edge of any plate made of cardboard sheet or another similar material although it is used for another type of foldable expanding device or even although it is not a plate for a foldable expanding device for maintaining a display upright.

A person skilled in the art is capable of introducing modifications and variations to the exemplary embodiments shown and described without departing from the scope of the present invention as it is defined in the attached claims.

The invention claimed is:

1. A display having an expanding device for maintaining the display upright, wherein said display (10) comprises three or more flat panels (11, 12, 13, 14) having lateral edges (15) connected to one another forming corners, and wherein said expanding device (200) comprises a plate (20) having a first hinge (21) dividing said plate (20) into first and second plate portions (20a, 20b), an elastic tensile element (7) pulling said first and second plate portions (20a, 20b) towards each other to fold the plate (20) around said first hinge (21) from a flat folded position to an angled working position, and at least one limiting member (23) which has a connection edge hingedly connected to the first plate portion (20a) by a second hinge (22) and a free edge (23a) which, when the plate (20) is in said angled working position, is in contact with the second plate portion (20b) in order to limit the folding of the plate (20) to said angled working position, wherein said second hinge (22) forms an angle greater than zero degrees with respect to said first hinge (21), and wherein the expanding device (200) is located between at least two adjacent flat panels (11, 12, 13, 14) forming a corner of the display (10) and the first and second plate portions (20a, 20b) of the expanding device (200) are connected to said two adjacent flat panels (11, 12, 13, 14) forming said corner of the display (10) in order to push from within the flat panels (11, 12, 13, 14) from a collapsed position, in which the flat panels (11, 12, 13, 14) have a flat arrangement, to an expanded position, in which the flat panels (11, 12, 13, 14) have a three dimensional arrangement capable of being held upright.

2. The display having an expanding device according to claim 1, wherein the first hinge (21) of the plate (20) is arranged substantially aligned with two of said lateral edges (15) connected to one another of the two adjacent flat panels (11, 12, 13, 14) which form this corner of the display (10).

3. The display having an expanding device according to claim 2, wherein the limiting member (23) has at least one first hook element (4), the second plate portion (20b) has at least one second hook element (5) and said elastic tensile element (7) is an elastic tensile ring hooked on said first and second hook elements (4, 5).

4. The display having an expanding device according to claim 2, wherein the limiting member (23) is a first limiting member (23) and the plate (20) comprises a second limiting member (25) which has a connection edge hingedly connected to the second plate portion (20b) by a third hinge (24) which forms an angle greater than zero degrees with respect to said first hinge (21) and a second free edge (25a) which, when the plate (20) is in said angled working position, interacts with said first free edge (23a) of said first limiting member (23) in order to limit the folding of the plate (20) to the angled working position.

5. The display having an expanding device according to claim 4, wherein said first and second free edges (23a, 25a) of said first and second limiting members (23, 25) are mutually crossed and are supported on each other when the plate (20) is folded in the angled working position.

6. The display having an expanding device according to claim 5, wherein the first limiting member (23) has at least one first hook element (4), the second limiting member (25) has at least one second hook element (5), and said elastic tensile element (7) is an elastic tensile ring hooked on said first and second hook elements (4, 5).

7. The display having an expanding device according to claim 3, wherein the limiting member (23) has a plurality of said first hook elements (4) formed therein that are located at different distances from said second hook element (5), the first hook elements (4) being selectable for regulating the tension of the elastic tensile element (7).

8. The display having an expanding device according to claim 1, wherein the first and second plate portions (20a, 20b) of the plate (20) are joined to two adjacent flat panels (11, 12, 13, 14) of the display (10).

9. The display having an expanding device according to claim 1, wherein the first plate portion (20a) of the plate (20) has a first end edge (26) opposite to the first hinge (21) connected to a corner of the display (10) formed by said lateral edges (15) of two of the adjacent flat panels (11, 12, 13, 14) of the display (10) and the second plate portion (20b) of the plate (20) has a second end edge (27) opposite to the first hinge (21) connected to another corner of the display (10) formed by the lateral edges (15) of another two of the adjacent flat panels (11, 12, 13, 14) of the display (10).

10. The display having an expanding device according to claim 9, wherein said first and second end edges (26, 27) of the first and second plate portions (20a, 20b) are hingedly connected to respective connection tabs (16) and an elastic connector ring (8) is arranged surrounding said connection tabs (16) of the plate (20) and surrounding inwardly-bent tabs (17) hingedly connected to the lateral edges (15) of the panels (11, 12, 13, 14) of the display (10).

11. The display having an expanding device according to claim 10, wherein said connection tabs (16) of the plate (20) have substantially the same length in the direction of height of the display as said inwardly-bent tabs (17) of the flat panels (11, 12, 13, 14) of the display (10).

12. The display having an expanding device according to claim 10, wherein the first and second end edges (26, 27) of the first and second plate portions (20a, 20b) are hingedly connected to the respective connection tabs (16) by groove lines in combination with cut lines which define separating members (16a) which are coplanar with the respective first and second plate portions (20a, 20b) and which project further from the first and second end edges (26, 27) when the connection tabs (16) are folded.

13. The display having an expanding device according to claim 4, wherein said first and second free edges (23a, 25a) of said first and second limiting members (23, 25) are mutually aligned with and hingedly connected to one another.

14. The display having an expanding device according to claim 13, wherein the first and second plate portions (20a, 20b) of the plate (20) are separated pieces which have respective adjacent edges (21a, 21b) hingedly connected to one another to form the first hinge (21).

15. The display having an expanding device according to claim 14, wherein said first and second adjacent edges (21a, 21*b*) of the first and second plate portions (20*a*, 20*b*) are hingedly connected to respective connection tabs (28) and an elastic connector ring is arranged surrounding said connection tabs (28) of the plate (20) and surrounding inwardly-bent tabs (17) hingedly connected to the lateral edges (15) of the panels (11, 12, 13, 14) of the display (10).

16. The display having an expanding device according to claim 15, wherein the first and second free edges (23*a*, 25*a*) of the first and second limiting members (23, 25) are hingedly connected to respective connection tabs (29, 30) which have respective opposing superimposed surfaces and respective first superimposed hook elements (31) and said elastic tensile element (7) is an elastic tensile ring hooked on said first hook elements (31) and on at least one second hook element (32) formed on at least one of the first and second plate portions (20*a*, 20*b*) or on at least one of inwardly-bent tabs (17) hingedly connected to the lateral edges (15) of the panels (11, 12, 13, 14) of the display (10).

17. The display having an expanding device according to claim 3, wherein said second hook element (5) comprises hook members (5*a*, 5*b*) formed on respective contiguous fins (52*a*, 52*b*), which are separated by a dividing cut (54) and connected to the second plate portion (20*b*) by respective opposing hooking hinges (53*a*, 53*b*), oblique with respect to said dividing cut (54) and divergent as they approximate the respective hook members (5*a*, 5*b*).

18. The display having an expanding device according to claim 17, wherein said dividing cut (54) is perpendicular to the first hinge (21).

19. The display having an expanding device according to claim 18, wherein said dividing cut (54) is oblique with respect to the first hinge (21) and is inclined towards the limiting member (23) and said free edge (23*a*) of the limiting member (23) has an angled outline which is coupled to said two fins (52*a*, 52*b*) of the second hook element (5) in an angled working position.

\* \* \* \* \*